United States Patent [19]
Hirsch et al.

[11] Patent Number: 5,643,341
[45] Date of Patent: Jul. 1, 1997

[54] SYSTEM AND METHOD FOR ON-SITE FORMULATION OF PERSONALIZED COLOR-MAINTAINING SHAMPOO PRODUCTS FOR INDIVIDUAL USERS

[75] Inventors: Leland Hirsch, Roslyn Heights; Michael Mazzei, Manhasset, both of N.Y.

[73] Assignee: Artec Systems Group, Inc., Roslyn Heights, N.Y.

[21] Appl. No.: 681,116

[22] Filed: Jul. 22, 1996

Related U.S. Application Data

[63] Continuation of Ser. No. 218,911, Mar. 28, 1994, abandoned.

[51] Int. Cl.$^6$ ............................................. A61K 7/13
[52] U.S. Cl. .................... 8/405; 8/441; 434/84; 434/100; 434/103
[58] Field of Search ................. 8/405, 400, 441; 434/98, 99, 100, 103, 84, 94; 510/119; 424/70.6

[56] References Cited

U.S. PATENT DOCUMENTS

| | | | |
|---|---|---|---|
| 660,363 | 10/1900 | Clarkson | 434/98 |
| 709,328 | 9/1902 | Jorgensen | 434/98 |
| 918,068 | 4/1909 | Maratta | 434/98 |
| 2,866,277 | 12/1958 | Wise | 434/98 |
| 2,878,590 | 3/1959 | Dodge | 434/103 |
| 3,192,117 | 6/1965 | Kaiser et al. | 8/405 |
| 3,815,265 | 6/1974 | DePauw | 434/103 |
| 4,294,293 | 10/1981 | Lorenz et al. | 366/267 |
| 4,725,316 | 2/1988 | Mahany, II | 106/288 B |
| 4,998,617 | 3/1991 | Ladd, Jr. et al. | 206/219 |
| 5,013,244 | 5/1991 | Davidson | 434/98 |
| 5,161,974 | 11/1992 | Bourges | 434/98 |
| 5,163,010 | 11/1992 | Klein et al. | 364/479 |
| 5,316,481 | 5/1994 | Louise et al. | 434/99 |

OTHER PUBLICATIONS

*Color Your Hair*, Peter Waters, 1984, pp. 94–99.
*Modern Salon*, Paul Mitchell, "Color to Go", Jun., 1993.
*Modern Salon*, Logics, Nov. 1993.
*Modern Salon*, Nexus, Dec. 1993.
*Modern Salon*, "Punchy Color", Redken, Nov. 1993, p. 188.
Clairol Inc., Natural Instincts™, 1994.

*Primary Examiner*—Christine Skane
*Assistant Examiner*—Caroline L. Dusheck
*Attorney, Agent, or Firm*—Morgan & Finnegan

[57] ABSTRACT

A system and method for the on-site formulation of a personalized hair color maintenance shampoo product. The system and method are used to produce on-site of the salon a hair color maintenance shampoo product which is appropriately tailored to the color and tone of each individual's hair. A database information chart containing formulations of stock colored shampoos is correlated to a pair of sequential axes representative of hair colors and tones. A mixing bottle is provided which is calibrated to the formulations on the chart to obtain a shampoo product tailored to the individual's hair tone and color. The system and method yield a hair color maintenance shampoo personalized to the hair of the individual; eliminates the need to maintain an inordinate stock of pre-mixed hair colored maintenance shampoos and colors; and eliminates the necessity for an individual user to experiment with various stock shampoos.

8 Claims, 2 Drawing Sheets

SYSTEM AND METHOD FOR ON-SITE FORMULATION OF PERSONALIZED COLOR-MAINTAINING SHAMPOO PRODUCTS FOR INDIVIDUAL USERS

This is a continuation of application Ser. No. 08/218,911, filed on Mar. 28, 1994, now abandoned.

FIELD OF THE INVENTION

This invention relates to a system and method for on-site formulation of personalized color-maintaining shampoo products for individual users, and more particularly, to a system and method for on-site formulation of personalized color-maintaining shampoo products for an individual user according to the hair tone of the user and to the particular coloring of the hair of the user.

BACKGROUND OF THE INVENTION

It is well appreciated that individuals often wish to cosmetically maintain the coloring of their hair, and oftentimes seek to alter the coloring of their hair, by various known hair coloring treatments. These treatments are typically not inexpensive and are frequently time consuming as well. Moreover, the chemicals employed in these treatments can be caustic and somewhat damaging to the hair. Thus, individuals who have had their hair color-treated are often desirous of prolonging the effects of the hair coloring treatment for as long a period as possible, and otherwise wish to keep the hair in as healthy a state as possible between visits to the colorist.

One way of prolonging the freshness of a hair coloring treatment and to otherwise preserve the condition of the hair is to use a hair color maintenance shampoo. Examples of such hair color maintenance shampoos include the various ARTec® Colorist Collection Color Enhancing Shampoos made for and sold by the ARTec® Systems Group, Inc. of Roslyn Heights, N.Y. Such hair color maintenance shampoos are typically formulated with a degree of coloring, so as to assist the individual in his attempt to prolong the duration of the coloring treatment.

One factor of great importance in formulating typical hair color maintenance shampoos is that they must be prepared giving consideration to at least two variables—the cosmetically altered or natural coloring of the client's hair, together with the tone of the hair. Encompassing the gamut of individual hair colors there exist a number of basic hair colors: brunette, blonde, red, and black. Within each of these color categories are various degrees of tones which a person's hair may possess. Thus, someone with brown hair can have tones varying from ash (a drab blue) to red to gold. For red colored hair, the tones can vary from burgundy to strawberry. For blonde colored hair, the tones can vary from ash (drab) to golden to platinum.

In order to provide an appropriate shampoo which will maintain the color treatment of a given individual's hair, then, various shampoo color formulations will need to be met depending upon the coloring of the hair and the tone associated with the hair. For instance, a hair maintenance shampoo for an individual having blond colored hair must be formulated differently depending upon whether that individual's hair tone varies from burgundy to strawberry.

To meet the varying needs of the gamut of potential individual hair tones and colorings, the current practice of most salons is to stock a large variety and quantity of pre-prepared hair color maintenance shampoos. Thus, salons are normally forced to anticipate the various combinations of hair tones and colorings, and the salon must stock a pre-prepared hair coloring maintenance shampoo for each of the various combinations.

Some salons have also attempted to modify stock shampoos as needed. One way is to have the customer purchase a plurality of stock shampoos and have the customer hand-mix the same at the point they are to be used in an effort to arrive at some mix appropriate for the hair color and tone of a particular customer. However, this is often an ad-hoc procedure, prone to much experimentation on the part of the colorist and client. Such efforts frequently result in a less than adequate formulation for the client that does not precisely match the color and tone of the client's hair. Moreover, the procedure is highly inaccurate, as the actual mix will typically be inconsistent each time the client prepares the formulation for its application to the hair.

As can well be imagined, then, the current practice is somewhat limited and presents problems both to the salon and to the client. Due to the abrasive nature of the color treatment, it is in the client's best interest to maintain the condition of the hair as healthy as possible between visits to the colorist. If the hair color is properly maintained, a colorist need only treat any new hair growth occurring between salon visits, and not the previously treated ends of the hair. If a properly matched shampoo is not employed, the previously treated portions of the hair will require additional treatment, leading to potential long-term hair damage, particularly if the treatments are continued often.

Moreover, to meet the varying shampoo needs, most salons are forced to carry large varieties and quantities of pre-prepared hair maintenance shampoos, thereby taking up valuable shelf and floor space (a particularly significant consideration in areas where retail store space is leased at a premium rate). There are numerous attendant inventory problems created for each salon seeking to maintain adequate stock of the appropriate pre-prepared shampoos and in anticipating the appropriate need for various of the pre-prepared shampoos, further adding expense and time to the effort of the salon. These problems, of course, will be greatly amplified where a chain or network of retail salons is involved, the inventory typically centrally stored and distributed to the affiliated retail outlets.

Finally, significant problems of creative control are presented to the colorist and client when only a stock number of pre-prepared hair color maintenance shampoos are available. It will be virtually impossible to keep on hand a prepared shampoo which exactly matches the color and tone of the client's hair. Certain customers will have more unique hair tones and/or more unique cosmetically altered colors or natural colors. For these cases, an appropriate pre-mixed hair color maintenance shampoo will be difficult to procure or will otherwise be unavailable to the colorist, leaving the colorist with the dilemma of somehow creating an adequate substitute color shampoo from the available premixed stock tailored to the customer, or otherwise forcing the customer to settle for a less than adequate shampoo from available stock. In severe cases, the customer will have to do without a color maintenance shampoo.

Overall, then, the current practice of advising the customer to experiment with various stock shampoos in a rote (trial-and-error) manner is quite inaccurate, resulting in much wasted shampoo and expense associated therewith. More often than not, the trial and error method consistently yields a less than adequate shampoo formulation for that individual's hair.

There exists a need, therefore, for a system and a method of preparing appropriate hair color maintenance shampoos on-site tailored both to the cosmetically altered or natural coloring of each customer's hair and to the tone of that individual's hair, which will produce a hair color maintenance shampoo precisely tailored to the customer's hair color and tone, which eliminates the inventory and stock problems associated with the current practice, which will permit the colorist a high degree of creative control in addressing the gamut of hair tones and colorings which will be encountered in practice, and which will address the ad-hoc experimentation customers currently practice to mix their own shampoos from stock offerings.

There are known in the prior art various industry-available dye color mixing applications. Rather than prolonging the freshness of the hair coloring treatment and maintaining the coloring treatment that has already been imparted to the hair, these applications are typically directed to the formulation of the color dyes themselves for their use in the actual salon hair coloring process.

For instance, a number of industry applications are directed to allowing a stylist to cross-reference a client's hair color level against either a hair tone or a desired color level, so as to permit the stylist to select a single pre-mixed color dye from a large quantity of different pre-mixed dyes that are shipped by the manufacturer of the system for use with the system. Typically, these dyes are then mixed with a so-called "generator" or "developer" to activate the color for the processing treatment. The stylist's choice of the single, appropriate pre-mixed dye product is sometimes governed by a chart which cross-references hair color level against hair tone or desired color level. The available pre-mixed dyes are listed at various locations on the chart, typically with a single, pre-mixed dye satisfying a small number of combinations, and often only one, of specific hair color level against desired hair color level or hair tone. Examples of such systems include the Logics International, Inc. "Color Facts" and "Attitudes" dye product-system; the Synaplex "Mid-Color" Ultra-Shine No-Lift Hair Color system; and the Wella "Color Charm" Liquid Cream Hair Color system.

Certain other color dye preparation systems provide the stylist with some degree of guidance to adapt certain particular pre-mixed dyes, or combinations thereof, so as to address a particular client's hair. These systems oftentimes extend to voluminous or otherwise cumbersome reference materials which must be utilized or cross-referenced in accordance with the base system. An example of such system is described in the Clairol Professional Encyclopedia, "Hair Color". For instance, the Clairol Encyclopedia refers to a so-called "Torrids" formulator chart cross-referencing a natural hair color against a desired hair color. The chart features a series of individual discrete boxes, each box representative of a single natural hair color level and a single desired hair color level, leading the stylist to select one or more hair dyes which can be used independently or mixed to some degree to meet that single natural hair color level and that single desired hair color level. Separate from the chart, the Encyclopedia provides the stylist with certain textual recommendation for use with the Torrids system, in advising of a custom dye formulation table listing for the stylist certain customized formulas of two or more volumetric quantities of color dyes. However, these recommendations tend to be for specific coloring instances only and are not tied to any particular organized methodology to prepare color dye mixes for any type of possible hair coloring situation. Various aspects of color dye mixing is also referenced in the Schwarzkopf Color Technical Manual (albeit without the provision of a chart correlating hair colors and tones) and in the Framesi 2001 Hair Color Training Manual.

As will be appreciated, most of the color dye systems employ a large number of pre-mixed color dyes. Typically, it is the intent of these systems that the stylist select a single pre-mixed dye from a large number used in the particular coloring system. Rather than maintain the freshness of a prior hair coloring treatment, the intent of these color dye systems is to select a color dye which will change the color of a person's hair, cover gray hair, or the like. In effect, then, these systems endeavor to make precise color for a very specific, narrow characteristic of a person's hair, not to continually hold or maintain or prolong the freshness of color already applied to a person's hair. While certain of the dye systems include some background information as to combining more than one pre-mixed dye to accommodate a particular colorist's need, the information is oftentimes not made integral with the bulk of the system. The information is typically embodied in a textual form separate and apart from the depictions used in the system, and the information is oftentimes limited to a discrete number of particular coloring applications, without any particular methodology or organization to guide the stylist to modifications across a wide gamut of potential hair coloring situations. Generally, then, owing to the existing concerns, the systems are not adapted to on-site preparation of a hair color maintainance shampoo product which can be utilized at home by a wide variety of customers.

There are also known in the prior art certain other systems for mixing proportions of materials to arrive at a desired mix. None of these systems, however, addresses the unique needs faced by the salon colorist in practice. For example, Morley, U.S. Pat. No. 1,744,328 is directed to a cocktail shaker. A transparent "body member" is provided having a depression molded therein. The depression accepts a formula strip which is calibrated for a particular cocktail to be made. The formula strip includes a series of gradations to proportion various ingredients for the specific cocktail. This provides the information necessary to mix a single cocktail on a single pre-printed strip, without a discernible way to vary and personalize the mix according to specific factors. The mixing system of Morley is thus intended to mix a single combination depending on the particular strip used.

Johnson, Jr., U.S. Pat. No. 3,948,105 is directed to a proportioning and mixing "graduate". A main liquid retaining compartment is provided in communication with a mixing compartment and a smaller liquid receiving compartment. Gradation marks are provided in the main compartment, with a "ratio array" of discrete graduated columns provided in the smaller compartment. The volume relationship between the large and small compartments is specifically predetermined in a manner such that the specific ratio of the main compartment content to the smaller compartment content is illustrated by the ratio-designating indicia at the upper end of each column of the array, when the number at the level of the liquid in the main compartment corresponds to a like number at the level of the liquid in any column of the ration array. An example is illustrated at Col. 3, lines 13–25 of the patent. However, Johnson, Jr. relates only to a bottle for offering a proper ratio mix of two liquids employing the so-called "ratio array" of fixed mixes. An indefinite number of liquid variations, matched to different conditions, cannot be achieved by the system of Johnson, Jr.

In a similar vein, Barnett, U.S. Pat. No. 4,292,846, also relates to a liquid proportioning container. A body portion constitutes the main reservoir of the container. The container includes a spout having calibrating marks at certain intervals. The spout is removable from the body portion to be filled to a desired level of fluid (in this case, oil). When the fluid is poured into the body portion and that body portion filled with the main liquid (in this case, gasoline), a desired fluid ratio will be attained. Again, as in Johnson Jr., no mention or suggestion is made of a system for formulating a wide variety of mixes.

In addition, certain systems are known to determine the color hue of a substance. For instance, Augur, U.S. Pat. No. 5,123,745, is directed to a system for determining the hue and value of a paint by a color wheel and gray scale. The system uses a bottle with a label designating certain bands of colors. The label may be rounded and would include twelve colors of a color wheel arrayed around the margin of the label. Each of the colors form an arcuate band on the label. The color bands extend to edges of the label to "bleed" into the color of a paint held in container, to aid the user to determine the color of paint, to choose complementary colors, or the like. While Augur provides a color matching system, no system is disclosed for measuring and mixing proportions of colors to obtain a personalized hair color shampoo, weighed against both the hair color and the natural hair tone.

Thus, it is an object of the present invention to provide a system and method for on-site formulation of hair color maintenance shampoo products which are personalized to the individual user.

It is a further object of the present invention to provide a system and method for on-site formulation of hair color maintenance shampoo products for individual users which are personalized to both the hair coloring of the individual user as well as to the tone of the individual's hair.

It is yet another object of the present invention to provide a system and method for formulating hair color maintenance shampoo products for individual users which may be produced on-site in the salon, thereby obviating inventory requirements and the need for maintaining a multifarious stock of pre-prepared color maintenance shampoo products.

It is still a further object of the present invention to provide a system and method for on-site formulation of hair color maintenance shampoo products for individual users to accommodate a wide variety of hair tones and colorings which can be easily modified by the colorist as desired, and which will yield a consistent product each time it is used by the customer that is appropriate for the individual's hair color and tone.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

These and additional objects are met by providing a system and method for on-site formulation of hair color-maintenance shampoo products according to the present invention. The method and system provides for on-site preparation of accurate individualized hair color maintenance shampoos, paying attention both to the particular hair coloring of a client's hair as well as to the tones of that client's hair. The method and system eliminate the need for a hair salon to keep a plurality of pre-mixed hair color-maintenance shampoos in stock for the gamut of hair tones and color types that can be imparted. Moreover, by providing for precise and consistent formulation of a hair color maintenance shampoo uniquely appropriate to the hair color and tone of the individual client, the method and system eliminates ad-hoc or rote experimentation by the client in seeking to tailor for himself an appropriate shampoo.

In accordance with one embodiment of the method and system of the invention, a pre-selected stock of basic colored shampoos can be mixed in precise combinations to accommodate each customer's hair tone and the coloring imparted to that hair. In accordance with the method and system of the invention, the precise combinations which will satisfy the spectrum of shampoo possibilities are embodied in a "database matrix" information chart containing directly thereon varied discrete formulations and combinations by which the colorist can correlate a proper combination (and quantities) of differing basic colored shampoos against both the hair tone and to the natural or cosmetically altered color of the hair to achieve a properly prepared shampoo. Typically, the discrete formulations extend across one or more client hair colors so as to facilitate and guide the stylist to adapt the formulas to a particular hair. By visual reference to the chart, the matrix formulations and combinations may be adjusted and/or revised by the colorist according to differing his/her experience to formulate a plurality of hair color maintenance shampoo products according to hair tones and/or hair colors. The formulations may also be revised taking into account hair porosity and its effects on certain stock shampoos, the trends of color impact rendered by certain stock shampoos in the formulation as the hair color varies, and the like. The information chart can be continuously upgraded or changed to accommodate new colors or advancements.

In accordance with the invention, the system and method further employs a mixing bottle having volumetric level gradations directly and precisely correlated against the formulations and combinations illustrated by the chart. The correlated mixing bottle will assist the colorist to derive an appropriate formulation of quantities and types of stock colored shampoos in order to prepare a desired color maintenance shampoo product.

The system and method will thus yield a personalized shampoo product, mixed onsite of the salon, that will greatly assist the individual to maintain the color and promote the health of her hair between visits to the colorist. In addition, the stylist may incorporate various conditioners with the personalized shampoo product, as needed or desired, so that the product will serve to condition the client's hair as it also cleanses the hair and maintains the color in the hair. The invention also eliminates the need for the salon to keep a wide variety of pre-prepared maintenance shampoos in stock, while providing the colorist with great latitude in deriving an appropriate product for each client's hair. The method and system also eliminates the need for ad-hoc or rote experimentation on the part of the customer or colorist. By employing, in combination, the precise formulation information embodied in the chart together with the specially calibrated mixing bottle, the customer will have a personalized shampoo with a consistent, precise formulation which will be useful in maintaining the specific hair coloring of the client's hair according to that customer's natural hair tone, as well as promoting the health of the hair.

The method and system may also be readily adapted to personalize other types of cosmetic hair care products. For instance, the principles embodied by the method and system may be used to formulate various types of hair conditioners or conditioning shampoo products, each readily adapted to one or more conditions of the client's hair. Thus, the method and system is widely adaptable to a wide range of salon needs which may be encountered.

DETAILED DESCRIPTION OF THE DRAWINGS

Figure 1:
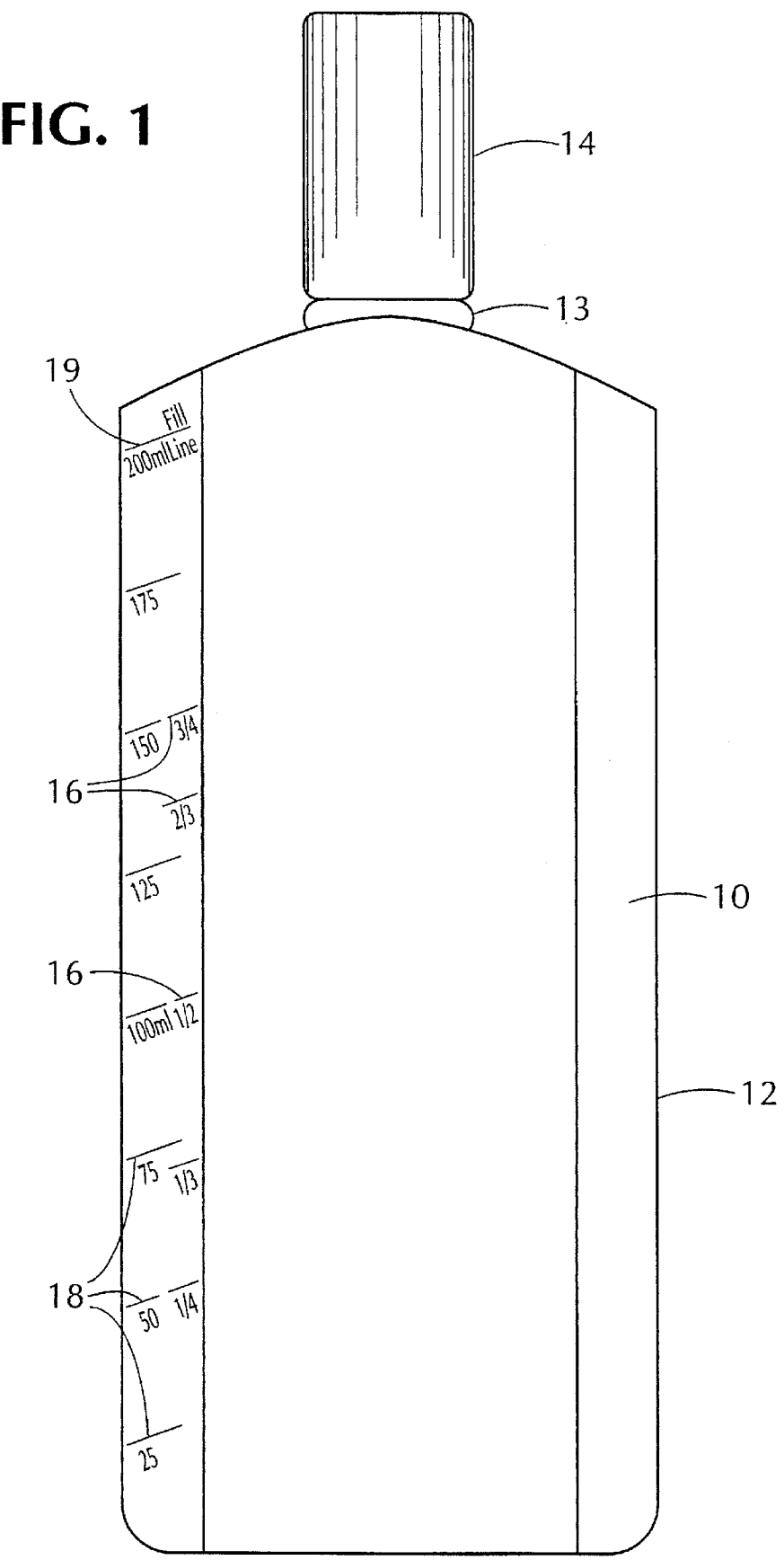
FIG. 1 illustrates a calibrated mixing bottle used in accordance with the system and method of the invention.
Figure 2:
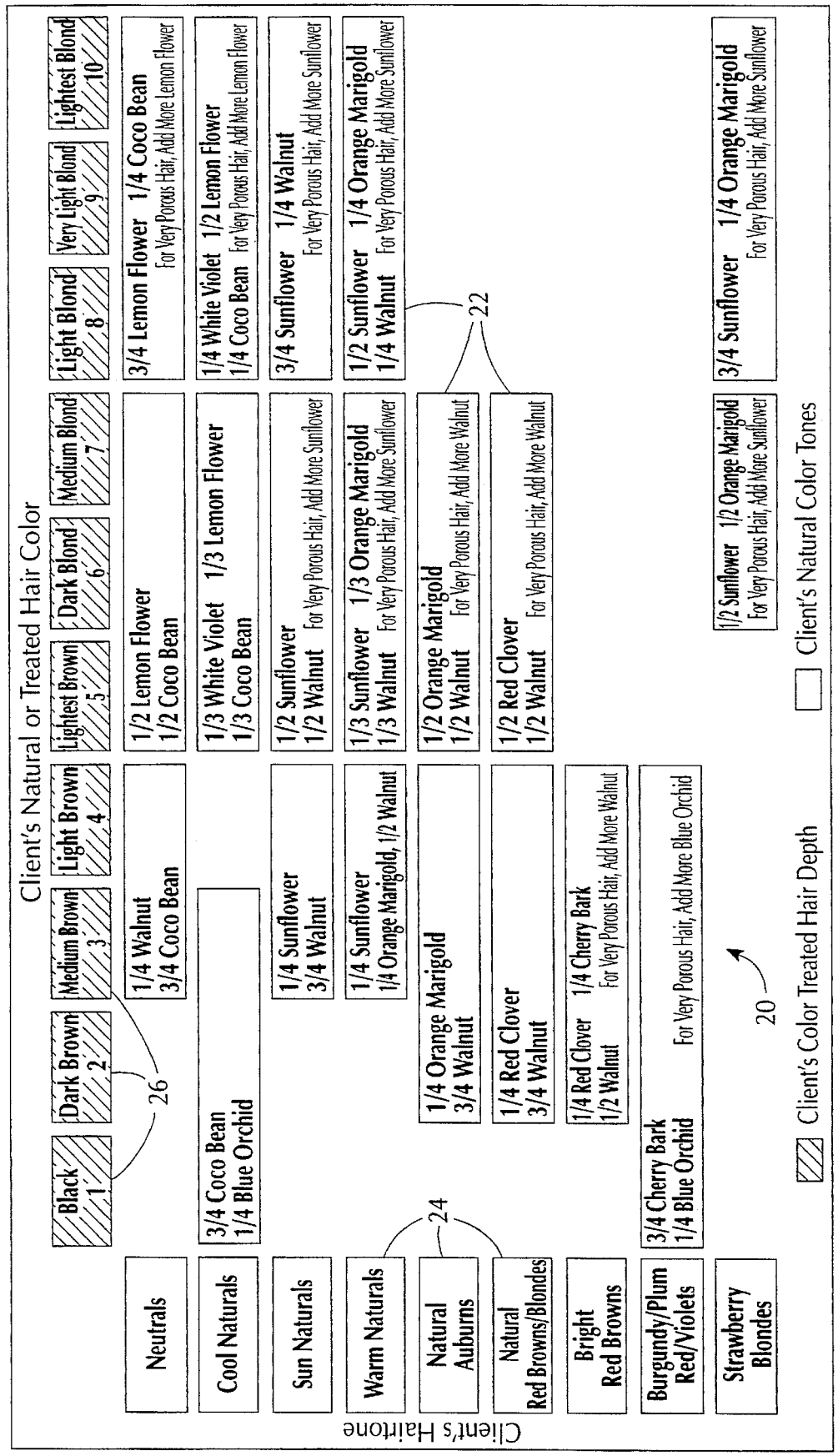
FIG. 2 illustrates a database information matrix chart used in conjunction with the calibrated mixing bottle of FIG. 1 in accordance with the system and method of the present invention.

Turning now to the drawings, wherein like numerals denote like components, FIGS. 1 and 2 illustrate a bottle 10 and a matrix information chart 20, respectively, utilized in accordance with the method and system of the invention. The bottle 10 includes a body portion 12 which may be molded or otherwise formed of plastic, glass or similar material, with the material forming the body portion 12 rendered clear or otherwise transparent in a manner to facilitate the colorist's view of the colored shampoos to be introduced into the bottle 10. The bottle 10 may also include an inlet portion 13 through which the shampoo is introduced into the bottle, with a cap portion 14 for dispensing the shampoo from the bottle.

As shown, bottle 10 may feature a plurality of volumetric measuring indicia 16 and 18 which are marked or otherwise formed onto the bottle 10 in a manner to provide a visible indication to the colorist. Indicia 16 may be calibrated to provide fractional volumetric designations relative to the overall capacity of the bottle (e.g., ¼ full, ⅓ full, ½ full, etc.). Similarly, indicia 18 may be chosen to provide volumetric fill indicia based on a standardized quantity of volumetric measurement (for example, milliliters (ml)). For reasons which will soon become apparent, a fill line 19 is indicated on the bottle so as to alert the colorist that the bottle has been filled to capacity with the colored shampoos to be introduced into the bottle. It will be understood to those skilled in the art that the indicia 16 and 18 may be chosen and marked onto bottle 10 to provide any desired combination of various fractional volumetric designations or standardized quantities of measurement, consistent with their calibration to the combinations and formulations provided by chart 20 in a manner which will now be described in better detail.

FIG. 2 depicts a database-matrix information chart 20 providing a number of formulations 22 correlated against the volumetric indicia of mixing bottle 10 for use in the method and system according to the invention. Thus, chart 20, in conjunction with the mixing bottle 10, includes a series of formulations 22 representative of desired formulations of basic colored shampoos to prepare a hair color maintenance shampoo product appropriate for a given individual's hair tone 24 and cosmetically altered or natural hair color 26.

Referring to FIG. 2, chart 20 includes a sequential categorization of differing hair colors 26 listed across the chart from a darkest color hue to a lightest color hue. For purposes of illustration and not of limitation, chart 20 here depicts the hair colors 26 ranging from blacks to blondes. To facilitate the colorist's derivation or modification of color formulations 22 as listed on the chart, the hair colors 26 may be listed in a numerically descending grade from a darkest hair color (black being 1) to a lightest hair color (lightest blonde being 10). As will become apparent, this orderly configuration of hair colors 24 will provide the colorist with a relative guide to altering formulations 22 to meet a particular client's hair color or tone.

On the vertical axis, the chart includes a sequential listing of hair tones 24 that are present and which describe the various tones of the hair. While the gamut of hair tones is extensive, the chart summarizes in a general fashion the color spectrum of underlying hair tones 24 which will be encountered by those skilled in the salon arts. In general terms, the various hair tones 24 can be characterized according to tonal base colors as will be recognized by those skilled in the art, as follows:

| Hair Tone 24 | Tonal Base Color |
| --- | --- |
| neutral | grey-violet tonal base color; |
| cool natural | blue-violet tonal base color; |
| sun natural | yellow-beige, brown or blonde tonal base color; |
| warm natural | yellow-orange, brown or blonde tonal base color; |
| natural auburn | orange-brown or blonde tonal base color; |
| natural red-browns/blondes | red-brown or blonde tonal base color; |
| bright red browns | red-violet tonal base color; |
| burgundy/plum, red/violets | blue-red - violet tonal base color; |
| strawberry blonde | yellow-orange - blonde tonal base color; |

Conveniently, the method and system according to the invention employs a stock number of various colored shampoos 28 which may be mixed in differing volumetric formulations 22 as depicted on to chart 20 to satisfy any hair color 26 or hair tone 24 associated with a particular customer. The use of only a relatively limited number of stock colored shampoos 28 conveniently permits the salon to eliminate oversupply of a large number of pre-mixed products. That is, each of the formulations 22 strives to define an appropriate volumetric mix of two or more stock colored shampoos 28 which will satisfy to produce a hair color maintenance shampoo appropriate to maintain the effects of and prolong the freshness of a hair coloring treatment for any given hair color 26 and underlying hair tone 24 as might be encountered by the stylist.

For convenience, each of the stock shampoos 28 described in the formulations 22 on FIG. 2 have been referred to by certain names descriptive of an overall color unique to each underlying color shampoo 28. In descriptive terms, the following stock shampoos 28 may possess the following descriptive color bases:

| Stock Shampoo 28 | Color Base |
| --- | --- |
| Walnut | (yellow orange or red) brown |
| Coco Bean | grey-violet brown |
| Lemon Flower | yellow-blonde |
| Sunflower | yellow-blonde (more yellow than blonde) |
| White Violet | blue-violet |
| Blue Orchid | blue grey-brown |
| Orange Marigold | orange |
| Red Clover | red |
| Cherry Bark | red-violet |

In order to achieve a proper color base, it has been found that each of the shampoos 28 utilized in the system and method of the invention may be individually formulated with one or more appropriate color dyes 30 that meet certain color standards established by the Cosmetics, Toiletries and Fragrance Association ("CTFA"). The combination of these dyes will produce the descriptive color tones of the individual stock shampoos 28 utilized in the method and system of the present invention.

While the scope of the invention is not limited to any particular quantity and/or particular stock shampoo 28, nor to any particular combination of dyes to arrive at appropriately derived color bases for each of the shampoos 28, the following is exemplary of dye formulations for imparting the appropriate color to the various stock shampoos 28.

colored shampoo 28 will bear in the various formulations 22 respective of the particular hair color and tone. The formulations 22 bear out the volumetric trends of stock shampoos 28 as the hair color 26 goes from dark to light (or vice-versa) so as to establish the relationship between volumetric quantities of stock shampoo 28 versus the color 24 and tone 26 of the hair. By incorporating this visual indication of color impact directly in the chart 20, the system and method according to the invention advantageously gives the colorist and client considerable and convenient guidance in tailoring the appropriate quantities and combinations of stock shampoos 28 in the formulations.

| | Shampoos 28 | | | | | | | | |
|---|---|---|---|---|---|---|---|---|---|
| Dyes 30 | | | | | | | | | |
| CTFA Name | Orange Marigold | Red Clover | Cherry Bark | Sunflower | Lemon Flower | Walnut | White Violet | Blue Orchid | Coco Bean |
| Basic Red 76 | X | X | | | | | | | |
| Basic Yellow 94 | X | | | | | | | | |
| Basic Blue 3 | X | | | | | | | | |
| Basic Red 104 | | | X | | | | | X | |
| Basic Brown 16 | | | | | | X | | | |
| Basic Brown 17 | | | | X | X | X | | X | X |
| Basic Blue 99 | | | | | | X | | X | X |
| Ext. D & C Violet No. 2 | | | | | | | X | | X |
| FD&C Blue No. 1 | | | | | | | | X | X |
| D&C Red No. 33 | | | | | | | | X | |
| HC Blue No. 2 | | | | | | | | X | X |
| HC Red No. 3 | | | | | | | | X | X |
| Basic Violet 1 | | | | | | | | | X |

Manufacturers of appropriate color dyes meeting these various CTFA standards are well known to those skilled in the art and may include, for example, the firms of Sandoz, Hilton Davis and Crompton & Knowles.

OPERATION OF THE INVENTION

Operation of the invention, utilizing the mixing bottle 10 and the information chart 20, is straightforward, and will now be explained by making reference to FIGS. 1 and 2.

A client may possess or otherwise have had his or her hair treated to a dark blonde color (unit 6 of color 26), the hair containing therein a Natural Auburn tone 24. Referring to FIG. 2, the colorist would deduce that for this particular combination of color and hair tone, an appropriate hair color maintenance formulation would include a shampoo containing one part stock orange marigold shampoo 28 and one part stock walnut shampoo 28. The hair color in maintenance shampoo would, thus, be formulated of equal quantities—i.e., one-half of each—of these stock shampoos 28. Referring to FIG. 1, the colorist would fill bottle 10 to the volumetric indicia 16 indicative of one-half full, starting with either orange marigold or walnut. Then, the colorist would fill the remainder of the bottle to the fill line 19 with the shampoo not previously chosen. Upon mixing the bottle 10, an appropriately formulated hair color maintenance shampoo for that particular customer will be obtained.

As previously indicated, by utilizing chart 20 in conjunction with the mixing bottle 10, the colorist is given considerable leeway in revising the formulations 22 of a particular hair color maintenance shampoo depending on the hair characteristics. Via the sequential ordering of colors 26 in descending color hue—here, from black to lightest blonde—the chart 20 attempts to correlate the impact that each stock This concept is best described by way of example. Referring to FIG. 2, the colorist may be confronted with a client whose hair tone 24 is Sun Natural, but whose hair color tends more to the blonde portion of the spectrum (i.e., the higher numbered colors 26 on the chart) than towards to darker (i.e., blacker/brown) colors on the spectrum. Referring to the chart, it may be seen that for such type hair, the colorist might wish to emphasize a more "yellowish" color tone stock shampoo 28 (i.e., Sunflower) than the darker tone shampoo 28 (i.e., Walnut). Thus, for lighter hair colors, the colorist is guided towards mixing a higher proportion of lighter colored shampoo 28 (here, Sunflower) than the darker colored shampoo 28 (here, Walnut). Similar trends may be detected, for example, for the Natural Auburn or Natural red brown-blonde hair tones 24, the lighter color tone shampoo being emphasized over the darker color tone shampoo as the hair becomes lighter in color.

Thus, the chart provides a ready medium to assist the colorist to derive proper formulations of stock colors 28 for the hair color maintenance shampoos depending on the hair color 26 and the hair tone 24 of the individual. It can be readily seen that the ad-hoc experimentation which was previously required by the colorist or client in deriving a proper shampoo for the particular hair is obviated, and through use of the uniform mixing system, a precisely regulated and mixed shampoo product is produced, eliminating the fluctuation of mixture which occurs when preparation of the shampoo was rendered.

It can also be seen that the chart 20 renders shampoo mixing information to the colorist and client, taking into account the porosity of the hair. As has been already explained, each of the formulations 22 contains some volumetric mixture of two or more stock shampoos 28. The color dilution effects which are obtained by mixing a lighter color hue shampoo (for example, Sunflower) with a darker color hue shampoo (for example Walnut) can be diminished if the shampoo is absorbed into the hair. Referring to FIG. 2, then, it can be seen that for certain hair colors, the chart will provide the colorist or client with guiding information regarding an appropriate color to emphasize in porous hair to compensate for the absorption effects of shampoo in the hair, all of which is necessary to properly maintain the color 26 of the hair.

For instance, for a dark blonde to light blonde hair color 26 with a sun natural tone 24 (i.e., a "golden blonde" hair), it may be seen that the absorptive effects of porous hair will prove more detrimental to the dilution of a darker color hue shampoo 28 (Walnut) with the lighter color shampoo (Sunflower). Referring to chart 20, to compensate for this dilution loss, the colorist will be guided as to adding more of the lighter colored shampoo (here, Sunflower) to the formula. As another example, for a Natural Auburn hair tone 24, it may be seen that the colorist will be guided to add more walnut over orange marigold to cut and dilute the brightness of the orange marigold, as the hair veers towards the blonder colors of the spectrum, the dilutive effects of the walnut shampoo diminished as the hair color 25 veers towards the blonder colors. It will be appreciated, then, that depending on hair color 26/hair tone 24, the colorist will be guided to adding more of the color hue shampoo whose color effects will be lessened as the overall shampoo formulation is absorbed by porous hair.

It will be understood, of course, that the principles taught herein are not solely applicable to formulating hair color maintenance shampoo products. The invention may be readily adapted to other cosmetic or similar products requiring personalized formulation, such as hair conditioners or styling aids, wherein attention to a plurality of variables is required in the personalized formulation. For instance, by mixing a stock quantity of colored conditioners, a colorist may produce a personalized hair conditioner product dependent on the individual's hair coloring and tone that, when used, would serve to prolong the coloring of a person's hair.

It will be apparent that other and further forms of the invention may be devised without departing from the spirit and scope of the appended claims, it being understood that this invention is not to be limited to the specific embodiments shown.

We claim:

1. A method of maintaining an individual's hair color and tone of previously color-treated hair comprising the steps of:

(1) determining an individual's hair color by visual recognition, wherein the individual's hair is color-treated, and wherein the hair color is selected from the group consisting of black, dark brown, medium brown, light brown, lightest brown, dark blonde, medium blonde, light blonde, very light blonde, and lightest blonde;

(2) determining an individual's hair tone by visually recognizing the individual's hair tonal base color, wherein the individual's hair is color-treated, and wherein the tonal base color is selected from the group consisting of grey-violet, blue-violet, yellow-beige, brown, blonde, yellow-orange, orange-brown, red-brown, red-violet, blue-red, and violet;

(3) referring to a chart which comprises two axes, wherein the first axis comprises said hair colors, and wherein the second axis comprises preselected hair tones based upon said hair tonal base colors;

(4) intersecting the individual's hair color on said first axis with the individual's hair tone on said second axis to determine a color maintenance shampoo formulation, wherein said hair color maintenance shampoo formulation comprises a mixture of at least two prepared hair color maintenance shampoos mixed in volumetric ratios according to said chart;

(5) mixing said at least two hair color maintenance shampoos in said volumetric ratios; and (6) contacting the individual's color-treated hair with the color maintenance shampoo formulation in order to maintain the hair color and tone of previously color-treated hair.

2. The method of claim 1 wherein the mixing step is performed with a bottle having volumetric fill indicia marked thereon correlated to the volumetric ratios of the formulation.

3. The method of claim 2 wherein the stock of two or more hair color maintenance shampoos are mixed by a colorist for later application by the individuals.

4. A method of maintaining an individual's hair color and tone of previously color-treated hair comprising the steps of:

(1) determining an individual's hair color by visual recognition, wherein the individual's hair is color-treated, and wherein the hair color is selected from the group consisting of black, dark brown, medium brown, light brown, lightest brown, dark blonde, medium blonde, light blonde, very light blonde, and lightest blonde;

(2) determining an individual's hair tone by visually recognizing the individual's hair tonal base color, wherein the individual's hair is color-treated, and wherein the tonal base color is selected from the group consisting of grey-violet, blue-violet, yellow-beige, brown, blonde, yellow-orange, orange-brown, red-brown, red-violet, blue-red, and violet;

(3) referring to a chart which comprises two axes, wherein the first axis comprises said hair colors, and wherein the second axis comprises preselected hair tones based upon said hair tonal base colors;

(4) intersecting the individual's hair color on said first axis with the individual's hair tone on said second axis to determine a color maintenance shampoo formulation, wherein said hair color maintenance conditioner formulation comprises a mixture of at least two prepared hair color maintenance conditioners mixed in volumetric ratios according to said chart;

(5) mixing said at least two hair color maintenance conditioners in said volumetric ratios; and (6) contacting the individual's color-treated hair with the color maintenance conditioner formulation in order to maintain the hair color and tone of previously color-treated hair.

5. The method of claim 4 wherein the mixing step is performed with a bottle having volumetric fill indicia marked thereon correlated to the volumetric ratios of the formulation.

6. The method of claim 5 wherein the stock of two or more hair color maintenance conditioners are mixed by a colorist for later application by the individuals.

7. The method of claim 1 wherein the hair color maintenance shampoo contains one or more dyes selected from the group consisting of basic red 76, basic yellow 95, basic blue 3, basic red 104, basic brown 16, basic brown 17, basic blue 99, Ext. D&C Violet No. 2, FD&C Blue No. 1, D&C Red No. 33, HC Blue No. 2, HC Red No. 3 and Basic Violet 1.

8. The method of claim 4 wherein the hair color maintenance conditioner contains one or more dyes selected from the group consisting of basic red 76, basic yellow 95, basic blue 3, basic red 104, basic brown 16, basic brown 17, basic blue 99, Ext. D&C Violet No. 2, FD&C Blue No. 1, D&C Red No. 33, HC Blue No. 2, HC Red No. 3 and Basic Violet 1.

\* \* \* \* \*